United States Patent [19]

Moore

[11] 4,402,984
[45] Sep. 6, 1983

[54] PREPARATION OF 1-HYDROPENTADECAFLUOROADAMANTANE AND PERFLUOROADAMANTANE

[75] Inventor: Robert E. Moore, Wilmington, Del.

[73] Assignee: Sun Tech, Inc., Philadelphia, Pa.

[21] Appl. No.: 358,559

[22] Filed: Mar. 16, 1982

Related U.S. Application Data

[62] Division of Ser. No. 165,902, Jul. 3, 1980, abandoned.

[51] Int. Cl.$^3$ ............................................. A61K 31/025
[52] U.S. Cl. ..................................... 424/352; 568/818; 570/126
[58] Field of Search ..................... 570/126, 130, 131; 568/818; 424/352

[56] References Cited

U.S. PATENT DOCUMENTS

| | | | |
|---|---|---|---|
| 3,911,138 | 10/1975 | Clark | 424/352 |
| 4,105,798 | 8/1978 | Moore et al. | 424/352 |
| 4,110,474 | 8/1978 | Lagow et al. | 570/130 |
| 4,113,435 | 9/1978 | Lagow et al. | 570/130 |
| 4,187,252 | 2/1980 | Lagow et al. | 570/130 |
| 4,289,499 | 9/1981 | Clark et al. | 424/352 |

FOREIGN PATENT DOCUMENTS

2079273  1/1982  United Kingdom ................ 424/352

OTHER PUBLICATIONS

Maraschin et al., "J. Amer. Chem. Soc.", vol. 97#3, pp. 513–517, (1975).
Robertson et al., "J. Organic Chemistry", vol. 43, #26, pp. 4981–4983, (1978).

*Primary Examiner*—Werren B. Lone
*Attorney, Agent, or Firm*—J. Edward Hess; Donald R. Johnson; Patrick C. Baker

[57] ABSTRACT

Perfluoroadamantane and 1-hydropentadecafluoroadamantane are prepared by perfluorinating adamantane and/or bromoadamantane by contacting $CoF_3$ at an elevated temperature. The fluoroadamantanes have utility as synthetic blood substitutes or perfusion media.

9 Claims, No Drawings

PREPARATION OF 1-HYDROPENTADECAFLUOROADAMANTANE AND PERFLUOROADAMANTANE

The invention described herein was made in the course of or under a contract with the U.S. Department of Health, Education and Welfare.

This is a division of application Ser. No. 165,902, filed July 3, 1980, now abandoned.

BACKGROUND OF THE INVENTION

This invention relates to a process for preparing perfluoroadamantane and 1-hydropentadecafluoroadamantane. More particularly, this invention relates to a process for converting adamantane or bromoadamantane to a mixture of perfluoroadamantane and 1-hydropentadecafluoroadamantane. The mixture can have utility as a synthetic blood substitute and/or a perfusion medium.

N. J. Maraschin et al. in J.A.C.S 97:3, 513–517 (Feb. 5, 1975) and G. Robertson et al. in J. Organic Chemistry, Vol 43, No. 26, 4981–4983 (1978) reports the preparation of 1-hydropentadecafluoroadamantane from adamantane using elemental fluorine ($-78°$ C. to room temperature) and requiring many hours. However, use of fluorine and a low temperature is not a viable commercial method for preparing large quantities in a short period.

Other processes involving perfluorination of cyclic hydrocarbons using $CoF_3$ are disclosed in the U.S. Pat. Nos. 4,143,079 and 4,105,798. These patents also disclosed the use of perfluorinated cyclic carbon compounds as synthetic blood substitutes or perfusion media. U.S. Pat. Nos. 4,110,474 and 4,187,252 disclose that perfluorinated methylpentanes are useful as synthetic blood substitutes and/or perfusion media. U.S. Pat. No. 3,911,138 discloses that certain perfluorinated cyclic carbon compounds, when emulsified, can be used as blood substitutes. The five aforementioned U.S. patents are incorporated herein by reference.

However, none of the foregoing art suggests that it would be possible to perfluorinate adamantane or bromoadamantane over $CoF_3$ without experiencing ring openings. Or that the resulting mixture of perfluoroadamantane and 1-hydropentadecafluoroadamantane would transpire from mice at a rate substantially greater than when using e.g., perfluorodecalin, a fluorocarbon considered by those skilled in the art as being a very good blood substitute.

SUMMARY

The process of this invention comprises contacting adamantane, bromoadamantane or a mixture of the two with $CoF_3$ at an elevated temperature. The process can be represented by the following reaction schemes:

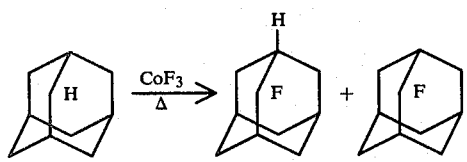

I

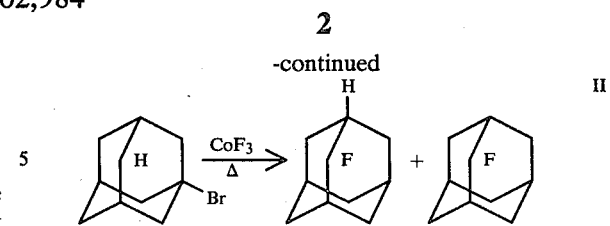

II in which "F" designates perfluorination. In reaction II the bromide atom can be located on the adamantane nucleus at positions other than shown in scheme II above. Perfluoroadamantane and 1-hydropentadecafluoroadamantane are useful as a synthetic blood substitute or a perfusion medium.

DESCRIPTION OF THE INVENTION

The process of this invention is for the preparation of a perfluoroadamantane and comprises fluorinating an adamantane selected from the group consisting of adamantane ($C_{10}H_{16}$), bromoadamantane ($C_{10}H_{15}Br$), and a mixture of the two. The fluorination involves contacting the adamantane with $CoF_3$ at an elevated temperature. The products resulting from the perfluorination of the adamantane include perfluoroadamantane and 1-hydropentadecafluoroadamantane.

One embodiment of carrying out schemes I and II is as follows. The adamantane is charged into a preheater by means of a Harvard infusion syringe pump. Since the feed adamantanes are solid at ambient temperature the feed is first dissolved in a suitable solvent such as hexane, for ease of handling, however, such solvents are not required. The preheater is maintained at a temperature sufficiently high to vaporize the adamantane and solvent prior to entering a reactor. The reactor itself is a horizontal $3.5'\times3''$ I.D. Monel tube containing 3500 gms of $CoF_3$ which is stirred by a series of paddles connected to a central shaft. The reactor is divided into four separate heating zones to allow it to be thermally graduated. More or less zones can work equally well.

Preferably, the material is passed through the reactor two times. The first pass is made with the reactor temperatures somewhat above the estimated boiling points of the materials being charged. As fluorination takes place, the boiling point of the product increases until 50% of the hydrogens have been replaced. Further fluorination causes a decrease in the boiling point of the product. The first pass is generally made at a moderate charge rate, desirably at a rate of 0.25 cc/min, with the reactor thermally graduated from just above the boiling point of the adamantane charge material i.e., 235° C. to approximately 50° C. above its boiling point. The second pass is made at considerably higher temperatures (approximately 100° C. greater across the reactor) to complete the fluorination.

The product is removed from the reactor through traced lines into a series of traps varying in temperature from 0° C. to $-78°$ C. which are designed not only to remove product but also HF and other gaseous products. A 3 to 4 hour nitrogen purge is required to remove all product from the reactor.

The $CoF_3$ used in the reaction can be regenerated by the technique disclosed in the aforementioned incorporated U.S. Pat. No. 4,143,079.

As indicated heretofore, the fluorination of the adamantane generally requires an elevated temperature which preferably exceeds the boiling point of the particular adamantane feed. Generally the fluorination will be at atmospheric pressure; however, if a lower pressure is used then a lower elevated temperature can be used.

As indicated previously the bromine atom can be located on the adamantane nucleus at positions other than that shown in aforementioned scheme II. While the structure in scheme II indicates the bromine atom is attached to a bridgehead carbon atom at position 1 other locations for the attachment will yield similar results. However attachment of the bromine atom to a bridgehead carbon atom is preferred.

Both the perfluoroadamantane and 1-hydropentadecafluoroadamantane are solid at ambient temperature. Thus the use of the aforementioned adamantanes as synthetic blood substitutes or perfusion media require that the adamantanes be dissolved in a suitable liquid fluorocarbon, examples of which include F-decalin, F-tricyclo[$5.2.1.0^{2,6}$]decane, F-methane (1-methyl-4-isopropylcyclohexane), F-1-methyldecalin, and F-alkyl adamantanes. The medical value of the aforementioned fluoroadamantanes lies in their ability to transport gases such as oxygen, carbon dioxide and carbon monoxide.

To further illustrate, the following examples are provided:

EXAMPLES

Five grams of solid adamantane (melting point 205° C.) were dissolved in 35 cc of liquid methylcyclohexane. Other suitable solvents include cyclohexane, dimethyl cyclohexane and the like. The resulting solution was pumped at 0.25 cc/min through the aforedescribed horizontal $CoF_3$ bed which was thermally graded from 240° C. to 275° C. between the inlet and outlet respectively. The resulting product was water washed to remove hydrofluoric acid and then dried. The dried product was then passed through the same reactor at a rate of 0.25 cc/min for a second time at a temperature varying from 250° C. to 300° C. The crude product weighed 25 g. Gas chromatographic analysis, IR, mass spec, and 19 FNMR showed this product to be a mixture of 1-hydropentadecafluoroadamantane and perfluoroadamantane. Both are solid at ambient temperature.

The foregoing procedure was repeated using 10 grams of bromoadamantane (melting point 116° C.) dissolved in 15 cc of n-hexane. The temperature of the reactor during the first pass was from 240° C. to 275° C., while during the second pass it was from 250° C. to 325° C. The crude product weighed 8.5 g. Analyses showed the product to be a mixture of 1-hydropentadecafluoroadamantane (90–92 wt.%) and perfluoroadamantane (8–10 wt.%). The two materials were separated using a 300 ft. capillary (3 wt.% hexadecane on Kel F polymer).

The resulting product mixture of 1-hydropentadecafluoroadamantane and perfluoroadamantane, dissolved in e.g., F-decalin and mixed with other suitable components, i.e., water and a surfactant, to form a suitable emulsion, was injected intraperitoneally into mice. The fluoroadamantanes were found to transpire from the bodies of the mice at a rate substantially greater than that obtained using perfluorodecalin in an emulsion.

I claim:

1. A liquid composition, useful as a synthetic blood substitute or a perfusion medium, comprising a normally solid component selected from perfluoroadamantane, 1-hydropentadecafluoroadamantane and a mixture thereof and which solid component is dissolved in a suitable liquid perfluorocarbon.

2. The composition of claim 1 wherein the solid component is said mixture of perfluoroadamantane and 1-hydropentadecafluoroadamantane.

3. The composition of claim 1 additionally containing water and a surfactant in amounts effective to emulsify said solid component and liquid perfluorocarbon.

4. The composition of claim 3 wherein the solid component is a mixture of perfluoroadamantane and 1-hydropentadecafluoroadamantane.

5. The composition of claim 3 wherein the solid component is perfluoroadamantane.

6. The composition of claim 3 wherein the solid component is 1-hydropentadecafluoroadamantane.

7. The composition of claim 1 wherein the liquid perfluorocarbon is selected from F-decalin, F-tricyclo[$5.2.1.0^{2,6}$] decane, F-menthane, F-1-methyldecalin and F-alkyl adamantanes.

8. The composition of claim 3 wherein the solid component is a mixture of perfluoroadamantane and 1-hydropentadecafluoroadamantane, and the liquid perfluorocarbon is selected from F-decalin, F-tricyclo [$5.2.1.0^{2,6}$] decane, F-menthane, F-1-methyldecalin and F-alkyl adamantanes.

9. The composition of claim 4 wherein the mixture contains 8–10 wt.% perfluoroadamantane and 90–92 wt.% 1-hydropentadecafluoroadamantane, and the liquid perfluorocarbon is F-decalin.

* * * * *